United States Patent
Johnson

(10) Patent No.: US 12,410,382 B2
(45) Date of Patent: Sep. 9, 2025

(54) DENTAL MATERIAL COMPOSITIONS FOR CLEANSING AND REMOVAL OF ANIONIC CONTAMINANTS FROM SUBSTRATES AND THEIR METHODS OF USE

(71) Applicant: INTER-MED, INC., Racine, WI (US)

(72) Inventor: Alexander D. Johnson, Racine, WI (US)

(73) Assignee: INTER-MED, INC., Racine, WI (US)

( * ) Notice: Subject to any disclaimer, the term of this patent is extended or adjusted under 35 U.S.C. 154(b) by 465 days.

(21) Appl. No.: 18/159,019

(22) Filed: Jan. 24, 2023

(65) Prior Publication Data

US 2023/0235248 A1    Jul. 27, 2023

Related U.S. Application Data

(60) Provisional application No. 63/267,074, filed on Jan. 24, 2022.

(51) Int. Cl.
| | | |
|---|---|---|
| C11D 3/04 | (2006.01) | |
| A61C 17/02 | (2006.01) | |
| A61C 19/00 | (2006.01) | |
| C11D 3/12 | (2006.01) | |
| C11D 3/40 | (2006.01) | |

(52) U.S. Cl.
CPC ............... *C11D 3/046* (2013.01); *A61C 17/02* (2013.01); *A61C 19/002* (2013.01); *C11D 3/124* (2013.01); *C11D 3/40* (2013.01)

(58) Field of Classification Search
USPC .......................................................... 424/49
See application file for complete search history.

(56) References Cited

U.S. PATENT DOCUMENTS

| | | | | |
|---|---|---|---|---|
| 3,538,230 | A | * | 11/1970 | Pader ................ A61K 8/315 |
| | | | | 424/57 |
| 3,906,090 | A | * | 9/1975 | Colodney ............. A61Q 11/00 |
| | | | | 424/49 |
| 4,218,434 | A | | 8/1980 | Rolla et al. |
| 5,915,969 | A | | 6/1999 | Linden |
| 8,951,506 | B2 | | 2/2015 | Sunkara et al. |
| 2020/0337970 | A1 | | 10/2020 | Dogo-Isonagie et al. |

FOREIGN PATENT DOCUMENTS

WO    2004055003 A1    7/2004

OTHER PUBLICATIONS

International Search Report and Written Opinion for International Application No. PCT/US23/61192, mailed Apr. 14, 2023, 8 pages.

\* cited by examiner

*Primary Examiner* — Walter E Webb
(74) *Attorney, Agent, or Firm* — Ryan L. Marshall; Barnes & Thornburg LLP

(57) ABSTRACT

Compositions and methods useful for removing anionic contaminates and debris including phosphates from dental restorative substrates are disclosed.

20 Claims, 1 Drawing Sheet

DENTAL MATERIAL COMPOSITIONS FOR CLEANSING AND REMOVAL OF ANIONIC CONTAMINANTS FROM SUBSTRATES AND THEIR METHODS OF USE

CROSS-REFERENCE TO RELATED APPLICATION

This application claims the benefit of U.S. Provisional Application No. 63/267,074, filed Jan. 24, 2022, the entire contents of this application is hereby incorporated by reference herein.

BACKGROUND

Dental restorations, including dental abutments, are typically manufactured from ceramic or metal materials, and used during various dental procedures as part of restoring the functionality of a patient's tooth or teeth. Generally, the industry trend is moving towards ceramic materials instead of metals. Prior to bonding these restorations in place, a "try-in" is performed to confirm proper fitment and occlusion within the patient's mouth. During this "try-in" process, the restoration often contacts the patient's bodily fluids (i.e. saliva, dentinal fluid, oral mucosal transudate, sulcus fluid, and blood, among others). Those fluids contaminate the surface of the restoration with constituents that have an affinity for the restoration. Specifically, the contaminants from the bodily fluid have an electrostatic affinity to the chemical make-up of the restoration material that results in the formation of various types of chemical bonds or intermolecular bonds between the contaminates from the bodily fluid and the restoration material.

Although proteins present in bodily fluids can adsorb to the restoration surface, the most problematic contaminants are orthophosphate ($PO_4^{-3}$), hydrogen phosphate ($HPO_4^{-2}$), and dihydrogen phosphate ($H_2PO_4^{-1}$) all of which covalently bond to surface atoms of the restoration material. Collectively these three anions are generally referred to as "phosphate" throughout the rest of the application. Such contaminants negatively affect the permanent bonding of the restoration material in the patient's mouth. It is imperative, therefore, to remove these contaminants from the restoration surface after "try-in", but before permanent bonding in the patient's mouth thereby improving functionality and longevity of the restoration.

There are conventional techniques used to remove contaminants in restoration procedures. One method is blasting the restoration surface with abrasive blasting agents that physically dislodge and remove the contaminants or the outer layer of contaminated restoration surface material, thereby also removing the contaminants. This technique, however, negatively affects the fit of the restoration, isn't intended for use on some veneer materials, and requires specific abrasive blasting equipment that might not be present in every dental operatory. Another method involves the use of a product called Ivoclean® by Ivoclar Vivadent (Amherst, NY, USA) disclosed in U.S. Pat. Nos. 9,752,107 and 10,995,306. Ivoclean® is a composition containing micron-sized insoluble particles in an aqueous carrier that mimic the substrate of dental ceramic restoration materials, such as zirconia oxide. By Le Chatelier's principle, or the equilibrium law, phosphate is indirectly removed from the contaminated restoration surface due to the system reacting to the presence of the newly added ceramic substrate contained within Ivoclean® (i.e. the micron-sized insoluble particles). The micron-sized insoluble particles, now contaminated, are then rinsed away. Ivoclean®, however, through these means cannot theoretically removal all phosphate contaminants as some will inevitably remain due to the system always reaching an equilibrium of phosphate contaminates on the restoration surface and on the micron-sized insoluble particles contained within Ivoclean®. Additionally, Ivoclean® can be cumbersome to use clinically due to its composition as the micron-sized insoluble particles settle to the bottom of the product's container. In order to be used clinically, the user must vigorously shake the product immediately before use to suspend the micron-sized insoluble particles in the aqueous carrier. Any delay from shaking the product to application results in reducing the quantity of micron-sized insoluble particles being administered which would further decrease the amount of phosphate contaminants removed from the restorative surface. In view of these deficient and others, there is a need in the art for alternative materials and methods to reduce contaminants during restoration procedures that interfere with restoration bonding and adhesion.

SUMMARY

In one aspect, a composition for removing anionic contaminants from dental restorative surfaces is disclosed. The composition includes at least one metal trihalide salt, at least one thickening agent, at least colorant, and water, wherein the pH of the composition is between 2 and 4.

In some embodiments, the composition retains its chemical stability for more than 60 days without the formation of a visible precipitate. In some embodiments, the at least one metal trihalide salt contains a metal element exhibiting an electronegativity value between 1.0 and 1.3. In some embodiments, the at least one metal trihalide salt dissolves in water forming at least one metal cations, wherein the at least one metal cations has a high affinity for phosphate. In some embodiments, the metal of the at least one metal trihalide salt has an atomic size between 125 pm and 215 pm. In some embodiments, the at least one metal trihalide salt comprises a lanthanum salt. In some embodiments, the at least one metal trihalide salt comprises lanthanum chloride hydrate. In some embodiments, the at least one metal trihalide salt comprises lanthanum chloride hydrate at a concentration between 20% and 40%. In some embodiments, the at least one thickening agent comprises polyvinyl alcohol. In some embodiments, the at least one thickening agent comprises fumed silica.

In some embodiments, the composition also includes a surfactant or blend of surfactants. In some embodiments, the composition also includes a humectant or humectants.

In some embodiments, the composition has a viscosity between 0.2 and 0.8 Pa·s. In some embodiments, the colorant is added in sufficient quantity to provide visual contrast when applied to a dental restorative surface.

In some embodiments, the composition consists of: lanthanum chloride hydrate at a concentration of 28% (wt/wt), polyvinyl alcohol at a concentration of 3.2% (wt/wt), a blend of FD&C yellow #5-6 and red #40 at a concentration of 0.5% (wt/wt), and deionized water.

In another aspect, a method of cleaning a dental restorative surface is disclosed. The method includes applying a cleaning solution as disclosed herein to a dental restoration surface, allowing the cleaning solution to dwell on the dental restoration surface for a period of time, and rinsing away the cleaning solution from the dental restoration surface, wherein the pH of the cleaning solution is between 2 and 4.

In some embodiments, the cleaning solution does not require shaking prior to application to the dental restoration surface, wherein, the cleaning solution chemically removes substantially all phosphate contaminates from the dental restoration surface; and, wherein, the cleaning solution is chemically stable for at least 60 days without the formation of a visible precipitate. In some embodiments, the dwell time is between 10 and 30 seconds.

In another aspect, a dental restoration kit, is disclosed. The kit includes a cleaning composition as described herein and application tips or application brushes. In some embodiments, the kit also includes a dental primer and a dental cement or a dental composite.

BRIEF DESCRIPTION OF THE DRAWINGS

The drawings illustrate the best mode presently contemplated of carrying out the disclosure.

DESCRIPTION

Figure 1:
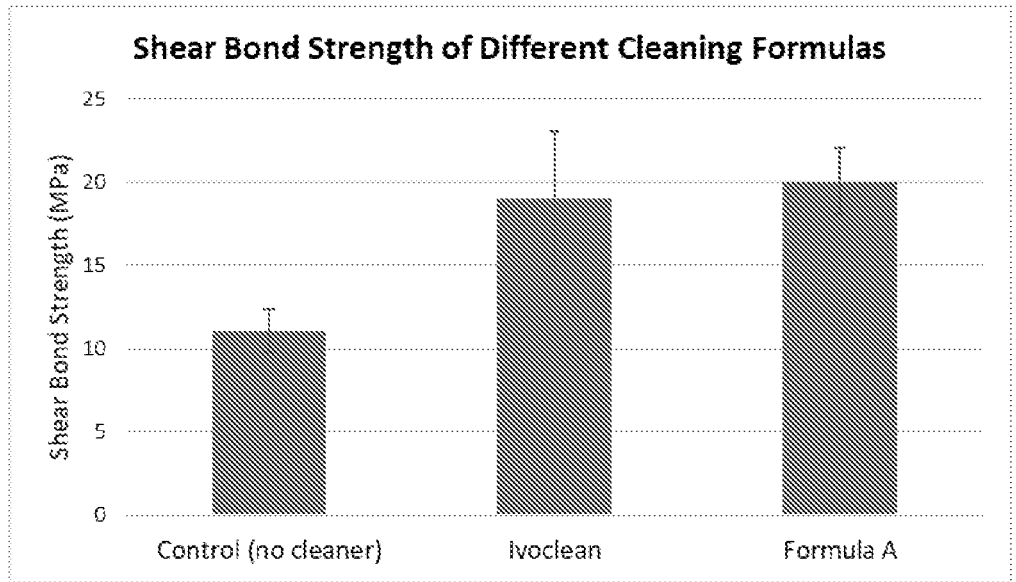
FIG. 1 displays shear bond strength measurements for Formula A, Ivoclean®, and no cleaner (control). As the results show, Formula A provided improved shear bond strength compared to the control group where contaminants were not removed.

The following paragraphs define in more detail the embodiments of the invention described herein. The following embodiments are not intended to limit the invention or narrow the scope thereof, as it will be readily apparent to one of ordinary skill in the art that suitable modifications and adaptations may be made without departing from the scope of the invention, embodiments, or specific aspects described herein.

An object of the present disclosure provides, within the framework of securing of dental restoration materials via bonding in a patient's mouth, a composition for the non-abrasive cleaning of restoration surfaces, in particular for removing anionic contaminants, that does not exhibit the aforementioned disadvantages of existing techniques. Specifically, a goal of this disclosure is to remove phosphate contaminates, however, practicing this disclosure will also sufficiently remove other anionic contaminate such as sulfates and proteins with an anionic charge, etc. Although much of the disclosure focuses on the extraoral cleaning of restorations, it is anticipated that the disclosure can additionally be used for various cleaning methods in vivo within the patient's mouth. The present disclosure also teaches methods utilizing the disclosed cleaning composition. The present disclosure furthermore relates to a method of inserting a dental restoration including a cleaning step using the disclosed cleaning composition.

In a specific embodiment, the cleaning composition is an aqueous solution comprising soluble cations with a high affinity for anions, such as phosphates, found in bodily fluids that contaminate restoration surfaces during "try-in" procedures. The soluble cations contained within the cleaning composition solubilize and remove the anionic contamination from a restoration surface. Through these means, the disclosed invention actually solubilizes the anionic contaminant for more effective and complete removal. In other words, the phosphate contaminant is not precipitated out of the aqueous solution or removed indirectly on an insoluble particle. Furthermore, the disclosed cleaning solution is easy to rinse from the restoration using water.

In order to achieve its effectiveness, the composition includes at least one water-soluble metal halide salt, which yields soluble cations in water, wherein the cation's element has an electronegativity value <2, preferably <1.5, even more preferably between 1.0 and 1.3, and most preferably about 1.1. The at least one water soluble metal halide salt is preferably at a weight/weight concentration (% w/w) between 1-90%, more preferably between 10-50%, and even more preferably between 20-40%. In some embodiments, the at least one soluble metal halide salts can be employed to yield various amounts of divalent, trivalent, or polyvalent cations in water. The atomic size of the at least one cation is preferably between 125-215 pm, more preferably between 150-215 pm, even more preferably between 175-200 μm, and most preferably is between 190-200 μm. In further embodiments, the at least one soluble metal halide salt is preferably a metal trihalide salt, such as a lanthanide halide salt including lanthanum chloride. In some embodiments, the at least one soluble metal halide salt is a hydrated salt.

The pH of the disclosed cleaning solution is preferably acidic (e.g. <7), more preferably between pH 1-5, even more preferably between pH 2-4, and most preferably between pH 3-4. In certain aspects, the at least one soluble metal halide salt yields at least one soluble cation that is not at a one-to-one (1:1) stoichiometric ratio with the anion contaminant. Without wishing to be bound to any particularly theory, it is believed that such a ratio mitigates potential precipitation formation during exposure to restoration contaminants. For example, at a slightly acidic pH (6.5), phosphate is present in an aqueous solution as both hydrogen phosphate ($HPO_4^{-2}$), and dihydrogen phosphate ($H_2PO_4^{-1}$). In order to mitigate potential precipitate formation, the disclosed compositions utilize a trivalent cation, such as lanthanum ($La^{+3}$) that would not result in a one-to-one (1:1) stoichiometric ratio with either phosphate anion, as the cationic and anionic charges do not match one-to-one. Although it is known that precipitations can still occur when these cations and anions are not at a one-to-one (1:1) stoichiometric ratio, this effort nonetheless mitigates undesirable precipitate formation.

In certain embodiments, the cleaning solution does not require shaking or mixing prior to use or application. The disclosed cleaning solution may be thixotropic and preferably has a viscosity of 0.01-2 Pa·s, more preferably 0.1-1 Pa·s, and most preferably 0.2-0.8 Pa·s. The cleaning solution has a preferred viscosity allowing it to spread out over the restoration surface but also retaining some thickness to ensure that the applied layer is sufficient in quantity to interact with contaminants on the surface. In other words, the cleaning solution is preferably semi-gel-like but still easily spreads across a restoration surface. In some aspects, the cleaning solution may be non-Newtonian or pseudoplastic. To achieve the target viscosity, the cleaning solution preferably contains a thickening agent/thickener at a concentration of 0.5-25% (wt/wt), more preferably 1-10% (wt/wt), and most preferably 2-5% (wt/wt). Examples of suitable thixotropic agents include fumed silica and metallic silicates. Examples of suitable thickening agents are polymers, such as polystyrene, polypropylene, polyethylene, polyacrylates, polyacrylamides, polyvinyl alcohol, fumed silica, and copolymers and surfactant combinations.

In some embodiments, the cleaning solution includes surfactants that decrease the solution's surface tension thereby facilitating easy spreading over the restoration surface. Preferably, the surfactants are cationic and/or non-ionic such that they do not interact with the metal cations in the cleaning solution. In further embodiments, the cleaning solution comprises a colorant, pigment or dye that provides visual contrast between the cleaning solution and the restoration material. The visual contrast helps the dental professional visually confirm adequate application of the cleaning solution to the entire restoration surface. The colorant, pigment, or dye should be chemically stable with the other cleaning solution constituents and not result in any chemical instability (i.e. precipitation formation, etc). In certain embodiments, the colorant, pigment or dye is a type of an azo dye or combination of azo dyes. Non-limiting examples of suitable dyes could include FD&C yellow #5, FD&C yellow #6, and FD&C yellow #40, or combinations thereof. In certain embodiments, the colorant, pigment or dye is not from the following types of chemicals: thiazine dyes, for example, methylene blue, or anthraquinone dyes, for example, D&C Violet #2 (also called Alizarine Violet 3B). In certain embodiments, the colorant, pigment or dye is not methyl orange, xylenol orange, D&C Violet #2, Violet 2185 (Koch Color, Bennett, CO), or Green PHS 2757 (Koch Color).

The cleaning solution may also comprise additional surfactants that enhance wetting, solubilization (solubility, cleaning and soil removal), debris suspension, emulsification and phosphate suspension. Examples of suitable wetting agents include cationic and nonionic surfactants, at an acidic pH, such as alkyldiphenyloxide disulfonates, alkyl aryl sulfonates, alkyl sulfates, alcohol ethoxylates, polyoxyethylene glycol octylphenol ethers, polyoxyethylene glycol alkylphenol ethers, polyoxyethylene glycol sorbitan alkyl esters, sorbitan alkyl esters, copolymers of polyethylene glycol and/or propylene glycol, Poloxamers, sodium sterates, sodium lauryl ether sulfates, linear alkylbenzene sulfonates, benzalkonium, benzethonium, methylbenzethonium, cetylpyridinium, alkyl-dimethyl dichlorobenzene ammonium, dequalinium and phenamylinium chlorides, cetrimonium and cethexonium bromides, betaines, primary or secondary or tertiary amines, octenidine dihydrochloride, fluorosurfactants, and amine oxides.

Hydrotropes can also be added to surfactants for formulation stability and to reduce phase separation. Certain hydrotropes that can be used in the cleaning solution include, but are not limited to, sodium xylene sulfonate (SXS), ethylhexyl sulfonate (EHS), and sodium cumene sulfonate (SCS), among others.

In certain embodiments of the disclosure, the cleaning solution comprises a metal halide salt, a thickener, a colorant or dye, and water. Optionally, the cleaning solution may further comprise a surfactant or blend of surfactants, and/or a humectant or humectants. Non-limiting examples of suitable humectants are glycerin, polypropylene glycol, sorbitol, or glyceryl triacetate, among others. Generally, all ingredients should exhibit transient biocompatibility for safety and toxicity considerations.

In principle, the disclosed cleaning composition can be used to clean all metal or ceramic surfaces, such as oxide and silicate ceramic, inside the patient's mouth (i.e. in vivo) or outside the patient's mouth (i.e. extraorally). The cleaning solution, however, is preferably used to clean clinically common dental restoration materials, such as titanium, gold, platinum group metals as well as their alloys and chromium-cobalt alloys, dental ceramics such as zirconium dioxide (zirconia), aluminum oxide and silicate ceramics, e.g. lithium disilicate glass ceramic, leucite glass ceramic, leucite apatite glass ceramic and feldspar ceramic.

In further aspects of the disclosure, the cleaning solution composition provides a suitable shelf life of preferably 6-48 months when stored at room temperature without displaying characteristics of chemical instability or significant decreased clinical efficacy. An example of chemical instability would be the formation of a precipitate during storage that renders the composition less effective (i.e. metal cations form a precipitate and are chemically unavailable for interaction with contaminants on a restoration surface) or useless (due to the precipitate potentially clogging various delivery or applicator tips thereby inhibiting application of the composition to the dental restoration surface).

The method of cleaning the dental restoration surface, or implant abutment, typically includes bringing the dental restoration surface into contact with the disclosed cleaning compositions described herein, and moving the cleaning composition on the surface, e.g. by distributing it over the surface (e.g. "rubbing" or "brushing") using a suitable instrument such as a brush or in the case of surfaces to be cleaned of small objects also by stirring the object in a liquid bath of the cleaning composition. Compared to the conventionally available Ivoclean® material, the disclosed compositions do not require mixing or shaking of the cleaning composition prior to application, thereby saving the dental professional a step in the cleaning process.

Optionally, a further step of leaving the cleaning composition to stand, or "dwell", on the surface can follow the aforementioned steps.

The cleaning composition is also removed in the restoration procedure, e.g. by rinsing with water and drying the surface with compressed air. The duration of the brushing cleaning step is preferably 5-60 seconds, particularly preferably 10-30 seconds. The duration of the standing or "dwelling" step is preferably 5-60 seconds, particularly preferably 5-30 seconds. The described method of cleaning then provides a substantially contaminant-free, dental restoration surface for bonding, cementing, or adhesively securing the dental restoration via traditional dental techniques and materials, such as the use of dental primers, dental adhesives, dental cements, and/or dental composites.

In some aspects, the cleaning solution may be packaged in a bottle sized between 0.1 mL-100 mL, and more preferably between 1 mL-10 mL. Alternatively, the cleaning solution may be supplied in various syringes sized between 0.1 mL-100 mL, and more preferably syringes sized between 0.5 mL-5 mL. Syringe packaging is more preferred as application tips can be mated directly to the syringes of cleaning solution for immediate application to the dental restoration surface. Conversely, the use of bottles requires an intermediate step of dispensing the cleaning solution into a mixing well, or other vessel, and then application to the dental restoration surface using various brushes or other means. In some embodiments of the invention, it may be beneficial to have the cleaning composition stored in separate containers (e.g. two separate bottles, dual barrel syringe, etc.) and mixed by the user immediately prior to use.

The packaging of the components must be compatible for long-term storage (months to years). Satisfactory plastic resins for the packaging material may include, but are not limited to, polypropylene, polyethylene, styrene acrylonitrile, methyl methacrylate-acrylonitrile-butadiene-styrene, poly-cyclohexylenedimethylene terephthalate glycol, among others.

In some aspects, the cleaning solution is provided as an item within a kit. In some embodiments, the kit may comprise any one or more of the following components: application tips, application brushes, mixing tips, mixing vessels, empty syringes, an instructions for use, mixing wells or other single use vessels, a dental etchant or etchants, a dental adhesive or adhesives, a dental primer or primers, a dental composite or composites, a dental cement or cements, among other common dental products.

Definitions

For purposes of interpreting this specification, the following abbreviations, terms and definitions will apply and whenever appropriate, terms used in the singular will also include the plural and vice versa. In the event that any definition set forth below conflicts with any document incorporated herein by reference, the definition set forth below shall control.

The term "room temperature" or ambient temperature as used herein refers to common ambient temperatures ranging from about 18° C. to about 27° C.

The term "treating" refers to administering a therapy in an amount, manner, or mode effective to improve a condition, symptom, or parameter associated with a disorder. In some aspects, treating refers to the treatment of a dental ailment such as an infected tooth.

The term "substantially" as used herein means to a great or significant extent, but not necessarily completely.

As used herein, "a", "an", "the", "at least one", and "one or more" are used interchangeably.

The term "patient" or "subject" refers to mammals and humans. Thus, in one aspect, the subject is a mammal, or a mammal in need thereof. In one aspect, the subject is a human, or human in need thereof. In one aspect, the human or human in need thereof is a medical patient. The subject can be from –0 years of age to 99 years of age or older.

The term "in vivo" generally means in a living subject.

The term "composition" generally refers to the chemical makeup of the disclosed cleaning solution and is synonymous with "formula".

The term "bonding" generally refers to cementing or adhesively securing the dental restoration to various structures within a patient's mouth.

The term "phosphate" generally refers to any of the following compounds: orthophosphate ($PO_4^{-3}$), hydrogen phosphate ($HPO_4^{-2}$), and dihydrogen phosphate ($H_2PO_4^{-1}$).

The term "dental restoration" or "restoration" generally refers to fabricated structures that may be used during various dental procedures to partially or fully restore the functionality of a patient's tooth or teeth.

The term "try-in" generally refers to the temporary placement of a dental restoration inside a patient's mouth (i.e. in vivo) to confirm proper fitment and occlusion prior to permanent bonding of the restoration within the patient's mouth.

The term "chemical stability" generally refers to a composition or formula that remains in chemical equilibrium for a period of time without significant reactivity. In some instances, this stability can be observed visually, for example, if there is not a change in the composition's state, such as observing the formation of a visible solid precipitate over time. Said differently, the observation of a visible precipitate within a composition or formula over time would indicate the initial formula was chemically instable. The precipitate then formed due to the composition desiring to became more chemically and thermodynamically stable.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

Examples

Table 1 below provides a range of ingredients that may be present in some aspects of a cleaning solution according to the present disclosure. Additionally, Table 2 provides example formulas or compositions for compositions of the disclosure.

TABLE 1

| Ingredient | Example | Preferred Concentration (w/w %) | More Preferred Concentration (w/w %) | Most Preferred Concentration |
|---|---|---|---|---|
| Metal halide salt(s) | Lanthanum chloride hydrate | 1-90% | 10-50% | 20-40% |
| Thickener(s) | Polyvinyl alcohol | 0-25% | 1-10% | 2-5% |
| Colorant(s) | FD&C red #40 | 0-5% | 0.0001-2% | 0.01-1% |
| Surfactant(s) | Fluorosurfactant | 0-5% | 0.01-2% | 0.1-1% |
| Water | Water | 10-95% | 25-85% | 50-85% |

TABLE 2

| Ingredient | Classification | Formula A (w/w %) | Formula B (w/w %) | Formula C (w/w %) |
|---|---|---|---|---|
| Lanthanum chloride hydrate | Metal trihalide hydrated salt | 28.0 | 28.0 | 28.0 |
| Polyvinyl alcohol | Thickener | 3.2 | 0.0 | 1.6 |
| Fumed silica (Aerosil 200) | Thickener | 0.0 | 1.5 | 0.8 |
| Blend of FD&C yellow #5-6 and red #40 | Colorants | 0.5 | 0.5 | 0.5 |
| Polysorbate 80 | Surfactant | 0.0 | 0.2 | 0.1 |
| Fluorosurfactant | Surfactant | 0.0 | 0.0 | 0.1 |
| Glycerin | Humectant | 0.0 | 0.0 | 35.0 |
| Deionized water | Water | 68.3 | 69.8 | 33.9 |
| pH | | 3.5 | 3.5 | 3.5 |
| TOTAL | | 100.0 | 100.0 | 100.0 |

To evaluate the performance of the disclosed cleaning solution, Formula A was subjected to a shear bond study. Briefly, a zirconia surface (10 mm diameter×5 mm height) was polished with 600 grit wet sandpaper, rinsed with deionized water, and air dried. Human saliva was applied to the polished surface for 30 seconds with agitation every 10 seconds followed by a deionized water rinse and drying with pressurized air. Formula A, Ivoclean®, or water (i.e. no cleaner solution; control) was then applied for the various test groups. A primer (ZrP™, Vista Apex, Racine, WI, USA) was then applied in two coats and air dried per the product's instructions for use. Superb™ adhesive (Vista Apex, Racine, WI, USA) was then applied, dried, and light activated for 10 seconds per the product's instructions for use. A cylindrical post of composite (Titan™ A2, Vista Apex, Racine, WI, USA) was created on the surface, using a mold, and light activating the Titan for 20 seconds to cure the composite. The shear bond strength of the composite post on the zirconia substrate was then measured after two hours using an Instron machine. Results are shown in FIG. 1 and demonstrate that Formula A provided improved shear bond strength compared to the control group where contaminants were not removed.

Figure 2:
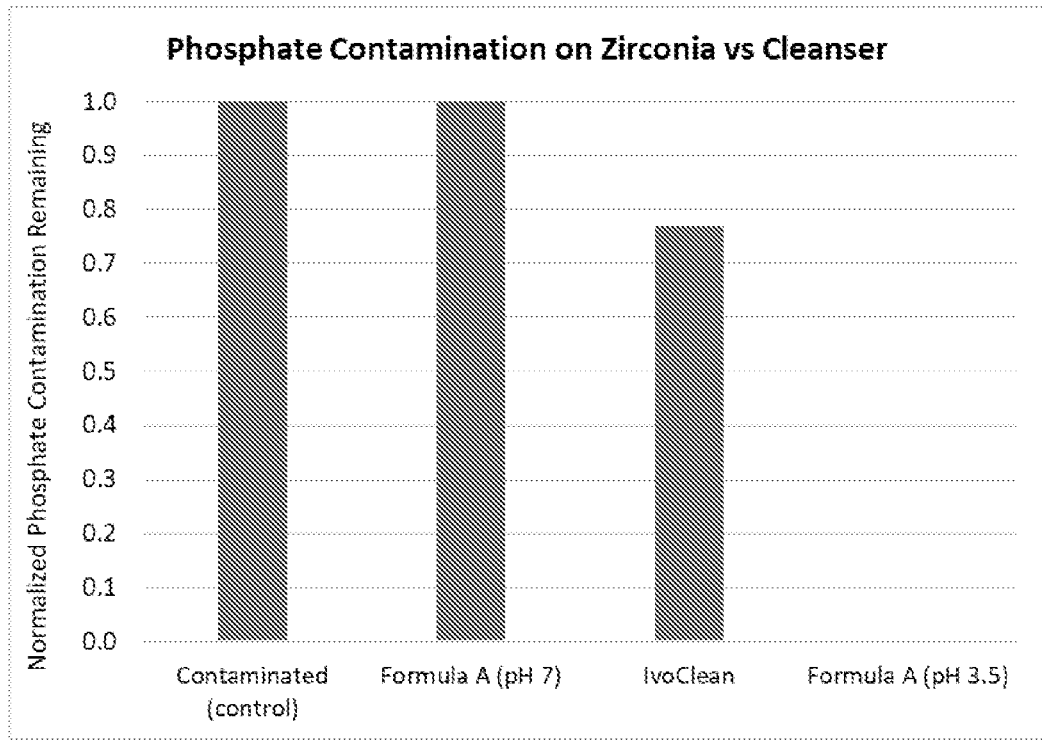
FIG. 2. displays XPS phosphate measurement results for zirconia surfaces subjected to no treatment (contaminated/control; water rinse only), Ivoclean®, Formula A (pH 7) and Formula A (pH 3.5). As the results show, Formula A at a pH of 3.5 was the only cleaning solution that was able to remove all phosphate contamination from the zirconia surface. Additionally, this test confirmed that the disclosed invention must have an acidic pH for proper removal of the phosphate contaminants from the ceramic surface.

To investigate the disclosed cleaning solution's ability to remove anionic, and more specifically phosphate contaminants, from dental restoration surfaces, an investigation using x-ray photoelectron spectroscopy (XPS) was completed. Briefly, zirconia restoration surfaces (10 mm diameter×5 mm height) were incubated in a 50 mg/dL hydrogen phosphate solution at a pH of 6.7 (to mimic saliva with excess phosphate) for three hours to allow for phosphate contamination of the zirconia surface. Following incubation, the zirconia surfaces were dried with pressurized, oil-free air. One test group, representing the control, was rinsed with ~5 mL of deionized water. For the other test groups (Ivoclean®, Formula A at a pH of 7, and Formula A at a pH of 3.5), approximately 2504 (~5 drops) of experimental cleaning solution was applied to the zirconia surface using an applicator brush (Vista Apex, Racine, WI, USA) for 10 seconds. The experimental cleaning solution was allowed to dwell for 20 seconds before a ~5 mL deionized water rinse and drying with pressurized, oil-free air. All samples were blinded and sent to Intertek (Allentown, PA, USA) for XPS analysis. Three XPS measurements were taken randomly on each zirconia surface to quantify the amount of phosphate present on the surface. Results are shown in FIG. 2 and demonstrate that Formula A at a pH of 3.5 was the only cleaning solution that was able to remove all measurable phosphate contamination from the zirconia surface without leaving any residue (e.g. lanthanum). Conversely, Formula A at a pH of 7 was unable to remove the phosphate contaminates, and surprisingly yielded measurable lanthanum cations debris on the zirconia surface due to adsorption. The neutral pH form of Formula A did not sufficiently remove phosphate contaminants from the surface.

Comparative Examples

Previous examples have illustrated unforeseen pH results observed through experimentation of the disclosed inventive cleaning solution composition. As additional comparative examples, Table 3 below lists formula compositions containing various dyes or pigments which were surprisingly found to be chemically unstable as a precipitate formed. For comparison purposes, a stable composition from Table 2 is additionally included. Initial review of the chemical structure of these dyes does not yield any readily apparent reason why they would not be compatible within the disclosed cleaning composition. For example, many of these dyes contain negatively charged functional groups (e.g., sulfonates), which could likely interact with the soluble metal cations in the disclosed composition at an acidic pH. However, it was discovered through testing that some of these types of dyes were compatible while others were not.

TABLE 3

| Ingredient | Classification | Formula A (w/w %) | Formula D1 (w/w %) | Formula D2 (w/w %) | Formula D3 (w/w %) | Formula D4 (w/w %) | Formula D5 (w/w %) | Formula D6 (w/w %) |
|---|---|---|---|---|---|---|---|---|
| Lanthanum chloride hydrate | Metal trihalide hydrated salt | 28.0 | 28.0 | 28.0 | 28.0 | 28.0 | 28.0 | 28.0 |
| Polyvinyl alcohol | Thickener | 3.2 | 3.2 | 3.2 | 3.2 | 3.2 | 3.2 | 3.2 |
| Dye | Colorant | 0.5 Blend of FD&C yellow #5-6 and red #40 | 0.5 (Methylene blue) | 0.5 (Methyl orange) | 0.5 (Xylenol orange) | 0.5 (D&C violet #2) | 0.5 (Violet 2185) | 0.5 (Green 5230) |
| Deionized water | Water | 68.3 | 68.3 | 68.3 | 68.3 | 68.3 | 68.3 | 68.3 |
| TOTAL (w/w %) | | 100.0 | 100.0 | 100.0 | 100.0 | 100.0 | 100.0 | 100.0 |
| pH | | 3.5 | 3.5 | 3.5 | 3.5 | 3.5 | 3.5 | 3.5 |
| Precipitation observed? | | No | Yes | Yes | Yes | Yes | Yes | Yes |
| Time precipitation observed | | N/A | <45 days | <20 days | <10 days | <30 days | <30 days | <60 days |

What is claimed is:

1. A composition for removing anionic contaminants from dental restorative surfaces, comprising:
   at least one metal trihalide salt;
   at least one thickening agent;
   at least colorant; and water
   wherein the pH of the composition is between 2 and 4.

2. The composition of claim 1, wherein the composition retains its chemical stability for more than 60 days without the formation of a visible precipitate.

3. The composition of claim 1, wherein the at least one metal trihalide salt contains a metal element exhibiting an electronegativity value between 1.0 and 1.3.

4. The composition of claim 1, wherein the at least one metal trihalide salt dissolves in water forming at least one metal cations, wherein the at least one metal cations has a high affinity for phosphate.

5. The composition of claim 1, wherein the metal of the at least one metal trihalide salt has an atomic size between 125 pm and 215 pm.

6. The composition of claim 1, wherein the at least one metal trihalide salt comprises a lanthanum salt.

7. The composition of claim 1, wherein the at least one metal trihalide salt comprises lanthanum chloride hydrate.

8. The composition of claim 1, wherein the at least one metal trihalide salt comprises lanthanum chloride hydrate at a concentration between 20% and 40%.

9. The composition of claim 1, wherein the at least one thickening agent comprises polyvinyl alcohol.

10. The composition of claim 1, wherein the at least one thickening agent comprises fumed silica.

11. The composition of claim 1, further comprising a surfactant or blend of surfactants.

12. The composition of claim 1, further comprising a humectant or humectants.

13. The composition of claim 1, wherein the composition has a viscosity between 0.2 and 0.8 Pa·s.

14. The composition of claim 1, wherein the colorant is added in sufficient quantity to provide visual contrast when applied to a dental restorative surface.

15. The composition of claim 1, wherein the composition consists of: lanthanum chloride hydrate at a concentration of 28% (wt/wt), polyvinyl alcohol at a concentration of 3.2% (wt/wt), a blend of FD&C yellow #5-6 and red #40 at a concentration of 0.5% (wt/wt), and deionized water.

16. A method of cleaning a dental restorative surface, comprising:
 applying a cleaning solution of claim 1 to a dental restoration surface;
 allowing the cleaning solution to dwell on the dental restoration surface for a period of time; and
 rinsing away the cleaning solution from the dental restoration surface,
 wherein the pH of the cleaning solution is between 2 and 4.

17. The method of claim 16, wherein, the cleaning solution does not require shaking prior to application to the dental restoration surface, wherein, the cleaning solution chemically removes substantially all phosphate contaminates from the dental restoration surface; and, wherein, the cleaning solution is chemically stable for at least 60 days without the formation of a visible precipitate.

18. The method of claim 16, wherein the dwell time is between 10 and 30 seconds.

19. A dental restoration kit, comprising:
 a cleaning composition of claim 1; and,
 application tips or application brushes.

20. The kit of claim 19 further comprising a dental primer and a dental cement or a dental composite.

* * * * *